United States Patent
Gosto et al.

(10) Patent No.: US 9,931,293 B2
(45) Date of Patent: Apr. 3, 2018

(54) COSMETIC COMPOSITIONS FOR MINIMIZING SKIN IMPERFECTIONS

(71) Applicant: L'OREAL, Paris (FR)

(72) Inventors: Sabina Gosto, Piscataway, NJ (US); Patricia Brieva, Manalapan, NJ (US); Donna McCann, Oxford, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/816,682

(22) Filed: Aug. 3, 2015

(65) Prior Publication Data
US 2017/0035680 A1    Feb. 9, 2017

(51) Int. Cl.
| | | |
|---|---|---|
| *A61K 8/87* | (2006.01) | |
| *A61K 8/85* | (2006.01) | |
| *A61K 8/73* | (2006.01) | |
| *A61Q 19/00* | (2006.01) | |
| *A61K 8/81* | (2006.01) | |

(52) U.S. Cl.
CPC .............. *A61K 8/87* (2013.01); *A61K 8/73* (2013.01); *A61K 8/8152* (2013.01); *A61K 8/8158* (2013.01); *A61K 8/85* (2013.01); *A61Q 19/00* (2013.01); *A61K 2800/262* (2013.01); *A61K 2800/48* (2013.01); *A61K 2800/594* (2013.01)

(58) Field of Classification Search
CPC ... A61K 8/87; A61K 8/85; A61K 8/73; A61K 8/81; A61Q 19/00
See application file for complete search history.

(56) References Cited

U.S. PATENT DOCUMENTS

| | | | |
|---|---|---|---|
| 2007/0036739 A1* | 2/2007 | Feng | A61K 8/91 |
| | | | 424/70.7 |
| 2007/0243220 A1* | 10/2007 | Sandewicz | A61K 8/85 |
| | | | 424/401 |
| 2008/0305069 A1 | 12/2008 | Cassin et al. | |
| 2010/0233222 A1 | 9/2010 | Girier Dufournier et al. | |
| 2011/0300092 A1* | 12/2011 | Kambach | A61K 8/8147 |
| | | | 424/70.7 |
| 2013/0142743 A1 | 6/2013 | Cavazzuti et al. | |
| 2014/0193351 A1 | 7/2014 | Mohammadi et al. | |
| 2014/0335136 A1 | 11/2014 | Brieva et al. | |

FOREIGN PATENT DOCUMENTS

| | | |
|---|---|---|
| FR | 2843025 A1 | 2/2004 |
| WO | 2012130690 A2 | 10/2012 |

OTHER PUBLICATIONS

"Veil Wrinkles: reveal your beauty", Centerchem, Inc. © 2013 http://www.centerchem.com/Products/DownloadFile.aspx?FileID=6530.
International Search Report and Written Opinion dated Oct. 4, 2016 re International Application No. PCT/US2016/044459.

\* cited by examiner

*Primary Examiner* — Sreeni Padmanabhan
*Assistant Examiner* — Jody Karol
(74) *Attorney, Agent, or Firm* — McNees Wallace & Nurick LLC

(57) ABSTRACT

The present invention relates to a cosmetic composition comprising (a) about 10% to about 20% by weight, based upon the total weight of the composition of a film forming agent; (b) about 1% to about 25% by weight, based upon the total weight of the composition of a particulate material; (c) two or more thickening agents; and (d) water. When applied to the skin, the composition allows for immediate tightening of the skin while decreasing the visibility of fine lines and deep wrinkles.

10 Claims, No Drawings

COSMETIC COMPOSITIONS FOR MINIMIZING SKIN IMPERFECTIONS

FIELD OF THE INVENTION

The present invention relates to a cosmetic composition comprising (a) about 10% to about 20% by weight, based upon the total weight of the composition of a film forming agent; (b) about 1% to about 25% by weight, based upon the total weight of the composition of a particulate material; (c) two or more thickening agents; and (d) water. When applied to the skin, the composition allows for immediate tightening of the skin while decreasing the visibility of fine lines, deep wrinkles, pores and skin imperfections.

BACKGROUND

As one ages, skin naturally becomes less elastic and more fragile. Fat in the deeper layers of the skin diminishes causing loose, saggy skin and more-pronounced lines and wrinkles.

Film forming agents are commonly used in cosmetic and skin care compositions intended to lessen the appearance of skin wrinkles by providing a smoothing and tightening effect. Film-forming agents are a group of chemicals that dry on the skin surface leaving a pliable, cohesive, and continuous thin coating. However, the use of film forming agents in cosmetic and skin care compositions may lead to negative attributes such as cracking, pilling, flaking, and leave a visible, white film on the skin.

Particulate materials are commonly used in cosmetic and skin care compositions intended to blur or diffuse the appearance of skin imperfections such as pores. Particulate materials serve to scatter light to achieve desirable optical effects. However, particulate materials can exaggerate the appearance of lines and wrinkles by accumulating inside the crevices. When used in combination with film forming agents, particulates may enhance the negative attributes of film forming agents.

Therefore, there has been a demand for development of a cosmetic composition capable of lessening the appearance of skin wrinkles and sagging, while at the same, having desirable cosmetic properties such as good texture and a translucent/transparent or natural appearance on the skin.

It has now been discovered that a cosmetic composition comprising: (a) about 14% to about 16% by weight, based upon the total weight of the composition of a film forming agent; (b) about 1% to about 25% by weight, based upon the total weight of the composition of a particulate material; (c) two or more thickening agents; and (d) water when applied onto skin, provides for an immediate tightening of the skin while decreasing the visibility of fine lines and deep wrinkles.

SUMMARY OF THE INVENTION

The present invention relates to a cosmetic composition comprising, in a cosmetically acceptable medium:
(a) about 10% to about 20% by weight, based upon the total weight of the composition of a film forming agent;
(b) about 1% to about 25% by weight, based upon the total weight of the composition of a particulate material;
(c) two or more thickening agents; and
(d) water.

The present invention also relates to a process of reducing the visibility of imperfections and/or imparting a homogenizing effect on skin, comprising applying the above-described composition onto the skin.

The invention also concerns a process comprising a step of applying at least one layer of the composition according to the invention onto the skin, in particular, the skin of the face.

In certain embodiments, the cosmetic composition of the invention is a skin care composition.

In other embodiments, the cosmetic composition of the invention is a make-up composition.

In a particular embodiment, the cosmetic composition of the invention is a base or a primer, in particular a skin care or a make-up base or primer. Thus, in certain embodiments, the cosmetic composition is applied as a base or a primer under a skin care product or a make-up product.

Preferably, the cosmetic composition of the present invention is in the form of one of the following: a skin care product, a make-up product (for example, a liquid foundation), a suncare product, a concealer product, a skin care or make-up base or primer composition. Preferably, the composition is an emulsion, such as for example, an oil in water emulsion.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 5% to 10% of the indicated number.

The term "skin" means the skin on the face or the lips or the skin around the eyes or the skin on the neck and chest areas or other parts of the body.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

"INCI" is an abbreviation of International Nomenclature of Cosmetic Ingredients, which is a system of names provided by the International Nomenclature Committee of the Personal Care Products Council to describe personal care ingredients.

"Volatile", as used herein, means having a flash point of less than about 100 degrees C.

"Non-volatile", as used herein, means having a flash point of greater than about 100 degree C.

"Cosmetically acceptable ingredients", as used herein, include waxes, preservatives, cosmetic active principles, moisturizing agents, UV screening agents, thickeners, water, surfactants, binders or fragrances.

According to the present invention, a homogenizing effect on the skin is to be understood as obtaining an even skin tone or color and/or producing a blurring/haze or soft focus effect on the skin such that the appearance of discolorations, blemishes, pores, fine lines or wrinkles is minimized by applying the compositions of the present invention. At the same time, the homogenizing effect imparted by the compositions of the present invention may be accompanied by a transparency effect wherein the compositions, once applied onto skin, do not produce an undesirable whitish sheen or film on the skin but are transparent/translucent such that the skin has a natural appearance.

A homogenizing effect according to the present invention can also be described in terms of the homogenizing power of the composition wherein the homogenizing power is measured in accordance with a protocol for measuring or evaluating the efficacy of the compositions with respect to minimizing the visibility of skin imperfections described below one said composition is applied onto skin. Homogenizing power may also be described as covering power.

The compositions and methods of the present invention can comprise, consist of, or consist essentially of the essential elements and limitations of the invention described herein, as well as any additional or optional ingredients, components, or limitations described herein or otherwise useful.

It was surprisingly and unexpectedly discovered that the compositions of the present invention, when applied onto skin, immediately tightened the skin while decreasing the visibility of fine lines and deep wrinkles. The compositions of the present invention can be characterized as having a homogenizing power such that when applied onto skin, the visibility of said lines and wrinkles was significantly reduced.

It was also surprisingly and unexpectedly discovered that when the compositions of the present invention were in the form of a skin care or a base or primer, the skin's natural complexion was unchanged, resulting in a bare skin or natural look appearance, while making it possible to be free of the use of foundation. This means that the compositions formed a coating or film that was sufficiently transparent such that said film or coating was not visibly noticeable.

Film Forming Agent

The term "film forming agent" means any ingredient that dries on the skin surface leaving a pliable, cohesive, and continuous thin coating. The film forming ingredients which may be used according to the invention are preferably chosen from interpenetrating polymers (IPN).

The term "interpenetrating polymer network" means a mixture of two interlaced polymers, obtained by simultaneous polymerization and/or crosslinking of two types of monomer, the mixture obtained having a specific glass transition temperature.

Interpenetrating polymer networks, or IPNs, are generally obtained by synthesis and/or crosslinking of the two polymers constituting them in the presence of each other, starting with monomers or prepolymers. In the case of a simultaneous polymerization of two types of monomer, the multifunctional monomers are chosen such that the polymerization mechanisms are different, so that the chain reactions develop independently of each other. When the two polymers are crosslinked, the product is a true IPN; crosslinking of only one of the polymers leads to a semi-IPN. In addition, the two polymers may be crosslinked with each other. These are then referred to as covalent IPNs.

Another process for preparing IPNs, known as the sequential process, consists in polymerizing a first monomer mixture in the presence of a crosslinking agent and of a preformed crosslinked polymer that is soaked with the monomer mixture and thus gradually swells as the polymerization reaction proceeds. The preformed crosslinked polymer must have a degree of crosslinking such that it can absorb at least ten times its weight of liquid.

IPNs are constituted of two intimately interlaced polymers, forming a three-dimensional network that cannot be associated by physical manipulation without breaking covalent bonds. The morphology of the network depends on the competition between the network formation kinetics and the phase separation kinetics.

Examples of IPNs that are suitable for use in the present invention, and also the process for preparing them, are described in patents U.S. Pat. Nos. 4,644,030 and 5,173,526, for example.

Preferably, the IPN according to the invention comprises at least one acrylic polymer and more preferentially also comprises at least one polyurethane.

According to one preferred form, the IPN according to the invention comprises a polyurethane polymer and a polyacrylic polymer. Such IPNs are especially those of the Hybridurz® series that are commercially available from the company Air Products.

Preferably, IPN sold by the company Air Products under the trade name Hybridur® 875 Polymer Dispersion (INCI name: polyurethane-2 (and) polymethyl methacrylate), or under the trade names Hybridur® 875 and Hybridur® 880.

The film forming agent is preferably present in the composition according to the invention in an amount of from about 5% to about 25% by weight, and preferably in an amount of from about 10% to about 20% by weight, based on the total weight of the composition.

Particulate Material

The term "particulate material" means colorless or white solid particles either of any shape or of a shape as specified herein which are in a form that is insoluble and dispersed in the medium of the composition. The particulate material which may be used according to the invention are preferably chosen from polymer particles.

Polymer particles suitable for use in the present invention are dispersible in water, with or without the assistance of a dispersing agent. According to certain embodiments, the polymer(s) that comprise the polymer portion have repeat units that include at least carbon and hydrogen, and optionally one or more of oxygen, silicon, nitrogen. According to certain embodiments, such polymer comprises a polyester or acrylic monomer. According to certain embodiments, the polymer comprising the polymer is crosslinked. According to certain other embodiments, the polymer particles are substantially spherical.

Polymer particles suitable for use in the present invention have an average particle size from about 0.5 microns to about 6 microns.

In the preferred embodiment of the invention, the polymer particles include a crosslinked polyester. One particularly suitable polyester is a polyester crosslinked with siloxane. The polyester may be formed by reacting a C4-C8 diacid with a branched C4-C6 diol, such as a polyester of adipic acid and neopentyl glycol crosslinked with isopropyltriethylsilane. A particular example of a suitable crosslinked polyester is a mixture of a polyester of adipic acid and neopentyl glycol crosslinked with isopropyltriethylsilane blended with a copolymer of vinyl pyrrolidone and vinyl acetate (INCI name adipic acid/neopentyl glycol crosspolymer) and is commercially available under the INCI name as AuraSphere™ N (containing about 50 percent total polymer) from Centerchem, Inc. of Norwalk, Conn. The polymer particles of AuraSphere™ N have a refractive index of 1.35 and a median particle size from about 0.5 to about 6 microns.

The particulate material is preferably present in the composition according to the invention in an amount of from about 1% to about 25% by weight, preferably in an amount of from about 4% to about 22% by weight, and most preferably about 5% to about 20% by weight, based on the total weight of the composition.

Thickening Agents

The two or more thickening agents of the present invention are preferably chosen from hydrophilic thickeners. The term "hydrophilic thickener" means a compound capable of increasing the viscosity of the aqueous phase of the composition.

Thickening agents suitable for use in the present invention be made of water-soluble or water-dispersible thickening polymers. They may in particular be chosen from polysaccharide biopolymers, crosslinked anionic acrylamide/AMPS copolymers, and mixtures thereof Non-limiting examples of polysaccharide biopolymers useful in the invention include, for example, xanthan gum, guar gum, gum Arabic, locus bean gum, acacia gum, scleroglucans, chitin derivatives and chitosan derivatives, carrageenans, gellans, alginates, or celluloses such as microcrystalline cellulose, carboxymethylcellulose, hydroxymethylcellulose, hydroxyethylcellulose and hydroxypropylcellulose.

A preferred polysaccharide biopolymer is xanthan gum.

When present in the composition according to the invention, the polysaccharide biopolymer is preferably present in the composition according to the invention in an amount of from about 0.01% to about 10.0% by weight, preferably in an amount of from about 0.01% to about 5.0% by weight, and most preferably about 0.01% to about 0.5% by weight, based on the total weight of the composition.

Non-limiting examples of crosslinked anionic acrylamide/AMPS copolymers useful in the invention include, for example, crosslinked anionic acrylamide/AMPS copolymers, in the form of a W/O emulsion, such as those sold under the name Sepigel™ 305 (INCI name: polyacrylamide (and) C13-14 isoparaffin (and) laureth-7) and under the name Simulgel™ 600 (INCI name: acrylamide/sodium acryloyldimethyltaurate copolymer (and) isohexadecane (and) polysorbate 80) by the company SEPPIC.

A preferred crosslinked anionic acrylamide/AMPS copolymers is polyacrylamide (and) C13-14 isoparaffin (and) laureth-7 which contains 40% polyacrylamide by weight, based upon the total weight of the emulsion.

When present in the composition according to the invention, the crosslinked anionic acrylamide/AMPS copolymers is preferably present in the composition according to the invention in an amount of from about 0.5% to about 15% by weight, preferably in an amount of from about 2% to about 10% by weight, and most preferably about 5% to about 7% by weight, based on the total weight of the composition.

Cosmetically Acceptable Medium

In addition to the ingredients indicated previously, a composition according to the invention comprises a cosmetically acceptable medium. In preferred embodiments, the cosmetically acceptable medium comprises water.

The term "cosmetically acceptable medium" is intended to denote a medium that is particularly suitable for applying a composition according to the invention to the skin.

The cosmetically acceptable medium is generally adapted to the nature of the support onto which the composition is to be applied, and also to the form in which the composition is to be packaged.

A composition of the invention may be a dispersion or an emulsion.

A dispersion may be made as an aqueous phase or as an oily phase.

An emulsion may have an oily or aqueous continuous phase. Such an emulsion may be, for example, an inverse (W/O) emulsion or a direct (O/W) emulsion, or alternatively a multiple emulsion (W/O/W or O/W/O).

In the case of emulsions, direct (O/W) emulsions are preferred.

Aqueous Phase

The composition according to the invention may comprise an aqueous phase.

The aqueous phase comprises water. A water that is suitable for use in the invention may be a floral water such as cornflower water and/or a mineral water such as Vittel water, Lucas water or La Roche Posay water and/or a spring water.

The aqueous phase may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol (C1-C4)alkyl ethers, mono-, di- or triethylene glycol (C1-C4)alkyl ethers, and mixtures thereof.

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants, and mixtures thereof.

The aqueous phase is preferably present in the composition according to the invention in an amount of from about 45% to about 90% by weight, preferably in an amount of from about 50% to about 85% by weight, and most preferably about 55% to about 80% by weight, based on the total weight of the composition.

Fatty Phase

A cosmetic composition in accordance with the present invention may comprise at least one liquid and/or solid fatty phase.

According to one embodiment, the composition according to the present invention is in the form of an emulsion.

In particular, a composition of the invention may comprise at least one liquid fatty phase, especially at least one oil as mentioned below.

The term "oil" means any fatty substance that is in liquid form at room temperature (20-25° C.) and at atmospheric pressure.

A composition of the invention may comprise a liquid fatty phase in a content ranging from about 1% to about 90%, in particular from about 5% to about 80%, in particular from about 10% to about 70% and more particularly from about 20% to about 50% by weight relative to the total weight of the composition.

The oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

The term "non-volatile oil" means an oil that remains on the skin at room temperature and atmospheric pressure.

More specifically, a non-volatile oil has an evaporation rate strictly less than 0.01 mg/cm2/min.

To measure this evaporation rate, 15 g of oil or of oil mixture to be tested are placed in a crystallizing dish 7 cm in diameter, which is placed on a balance in a large chamber of about 0.3 m3 that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm2) and per unit of time (minutes).

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm2/min, limits included.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Volatile Oils

The volatile oils may be chosen from hydrocarbon-based oils containing from 8 to 16 carbon atoms, and especially C8-C16 branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) (8×10-6 m2/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethyl-cyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane and dodecamethylpentasiloxane, and mixtures thereof.

When present in the composition according to the invention, the volatile oil is in an amount ranging from about 1% to about 80% by weight, preferably from about 5% to about 70.0% by weight, and most preferably from about 15% to about 35% by weight, relative to the total weight of the composition.

Non-Volatile Oils

The non-volatile oils may be chosen especially from non-volatile hydrocarbon-based, fluoro and/or silicone oils.

Non-volatile hydrocarbon-based oils that may especially be mentioned include:

- hydrocarbon-based oils of animal origin, such as perhydrosqualene,
- hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof, or alternatively caprylic/capric acid triglycerides, such as those sold by the company Stearineries Dubois or those sold under the names Miglyol® 810, 812 and 818 by the company Dynamit Nobel,
- linear or branched hydrocarbons of mineral or synthetic origin, such as liquid paraffins and derivatives thereof, petroleum jelly, polydecenes, polybutenes, hydrogenated polyisobutene such as Parleam, and squalane;
- synthetic ethers containing from 10 to 40 carbon atoms;
- oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from:
  - lipophilic polymers,
  - silicone oils,
  - oils of plant origin, and
  - mixtures thereof;
- optionally partially hydrocarbon-based and/or silicone fluoro oils, for instance fluorosilicone oils, fluoropolyethers and fluorosilicones as described in document EP-A-847 752;
- silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and
- mixtures thereof.

According to one particular embodiment, the fatty phase of the composition according to the invention can contain only volatile compounds.

According to another particular embodiment, the fatty phase of the composition according to the invention can contain non-volatile oils, preferably, in a total amount of not more than about 20% by weight, preferably, not more than about 10% by weight, or more preferably, not more than about 5% by weight, based on the total weight of the composition.

When present in the composition according to the invention, the non-volatile oil is in an amount ranging from about 1% to about 20% by weight, preferably from about 1% to about 10% by weight, and most preferably from about 1% to about 5% by weight, relative to the total weight of the composition.

Colorant

A composition according to the invention may also comprise at least one colorant.

A composition in accordance with the invention may incorporate at least one colorant chosen from mineral or organic pigments conventionally used in cosmetic compositions, liposoluble or water-soluble dyes, and mixtures thereof.

The term "pigments" should be understood to mean white or coloured, inorganic or organic particles which are insoluble in an aqueous solution and are intended for colouring and/or opacifying the resulting film.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate. According to one particular mode of the invention, the mineral pigments will be chosen from iron oxides and titanium oxides, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colorant may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP 0 542 669, EP 0 787 730, EP 0 787 731 and WO 96/08537.

The cosmetic composition according to the invention may also comprise water-soluble or fat-soluble dyes. The liposoluble dyes are, for example, Sudan red, DC Red 17, DC Green 6, β-carotene, soybean oil, Sudan brown, DC Yellow 11, DC Violet 2, DC Orange 5 and quinoline yellow. The water-soluble dyes are, for example, beetroot juice and caramel.

When present in the composition according to the invention, the colorant is in an amount ranging from about 0.25% to about 20% by weight, preferably from about 0.25% to about 10% by weight, and most preferably from about 0.25% to about 5% by weight, relative to the total weight of the composition.

Additives

A composition according to the invention may also comprise any additive usually used in the field under consideration, chosen, for example, from waxes, dispersants, antioxidants, essential oils, preserving agents, fragrances, neutralizers, antiseptics, UV-screening agents, cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the invention such that the desired cosmetic properties and stability properties thereof are not thereby affected.

A cosmetic composition of the invention may be in the form of a skin makeup product, in particular a foundation, a hot-cast foundation product, a body makeup product, a concealer, or an eyeshadow. It may be in the form of cream, lotion or soft paste.

A care composition according to the invention may in particular be a sunscreen or a moisturizing composition.

Preferably, the composition according to the invention is in the form of a fluid primer or base or a fluid foundation. When the composition is a foundation, it further contains at least one colorant as described above in an amount sufficient to provide additional color to or change the color of the skin.

In a particular embodiment, the composition is an emulsion. Such emulsions will generally be comprised of the liquid fatty phase (also known as an oil phase) and the aqueous phase as described earlier.

The invention also concerns a process comprising a step of applying at least one layer of the composition according to the invention, onto the skin, in particular the skin of the face.

In a particular embodiment, the composition is applied alone or as a base or primer under a skin care product or a makeup product.

The process is particularly intended to minimize or decrease the visibility of skin imperfections, in particular, lines and wrinkles.

In accordance with these preceding preferred embodiments, the compositions of the present invention are applied topically to the desired area in an amount sufficient to minimize the visibility of skin imperfections, care for and/or enhance the appearance of skin. The compositions may be applied to the desired area as needed, preferably once or twice daily, more preferably once daily. When the composition is applied onto skin as a primer or a base, then it may be allowed to dry before a subsequent composition is applied onto the skin. Preferably, the composition is allowed to dry for about 1 minute or less, more preferably for about 45 seconds or less. The composition is preferably applied to the desired area that is dry or has been dried prior to application.

The compositions of the present invention, such as for example, those which are employed as a foundation containing colorants, may also be applied onto skin to which a basecoat or primer has been previously applied.

The composition according to the present disclosure may be manufactured by the known processes generally used in cosmetics and personal care products.

The composition may be packaged in a jar or a bottle, which may be equipped with a pump mechanism for delivering the composition onto the skin or the fingers/hand.

The packaged composition may also be accompanied by an applicator device which allows the composition to be taken up and also allows the composition taken up to be deposited on the skin.

When a composition according to the present invention is applied onto skin, the composition has a homogenizing effect on skin, that is, the composition eves the skin tone or color and/or produces a blurring/haze or soft focus effect on the skin such that the appearance of discolorations, blemishes, pores, fine lines or wrinkles is minimized.

At the same time, the composition of the present invention does not produce an undesirable whitish sheen or film on the skin but is transparent/translucent such that the skin has a natural appearance.

A homogenizing effect according to the present invention can also be described in terms of the homogenizing power of the composition as described below.

EXAMPLES

TABLE 1

Examples

| Phase | US INCI Name | Inventive Examples | | | | Comparative Examples | |
|---|---|---|---|---|---|---|---|
| | | Ex. 1 | Ex. 2 | Ex. 3 | Ex. 4 | Ex. 5 | Ex. 6 |
| A | WATER | QS | QS | QS | QS | QS | QS |
| A | CHLORPHENESIN | 0.3 | 0.3 | 0.3 | 0.3 | 0.3 | 0.3 |
| A | CAPRYLYL GLYCOL | 0.4 | 0.4 | 0.4 | 0.4 | 0.4 | 0.4 |
| A | PHENETHYL ALCOHOL | 0.3 | 0.3 | 0.3 | 0.3 | 0.3 | 0.3 |
| B | GLYCERIN | 0.5 | 0.5 | 0.5 | 0.5 | 0.5 | 0.5 |
| B | XANTHAN GUM | 0.2 | 0.2 | 0.2 | 0.2 | 0.2 | 0.2 |
| C | POLYACRYLAMIDE (and) C13-14 ISOPARAFFIN (and) LAURETH-7 Sepigel ™ 305 40% Polyacrylamide, 21% C13-14 isoparaffin, and 7% laureth-7 in water | 6.0 | 6.0 | 6.0 | 6.0 | 6.0 | 6.0 |
| D | WATER | QS | QS | QS | QS | QS | QS |
| F | TITANIUM DIOXIDE (and) MICA | 0.5 | 0.5 | 0.5 | 0.5 | 0.5 | 0.5 |
| G | POLYURETHANE-2 (and) POLYMETHYL METHACRYLATE Hybridur ® 875 | 15.0 | 10.0 | 5.0 | 15.0 | 15.0 | 0 |
| G | ADIPIC ACID/NEOPENTYL GLYCOL CROSSPOLYMER AuraSphere ™ N | 5.0 | 10.0 | 20.0 | 20.0 | 0 | 5.0 |
| | TOTAL | 100 | 100 | 100 | 100 | 100 | 100 |

In making each of the examples in Table 1, the following procedure was used: The ingredients of phase A were added to the main kettle, heated to 75 to 80° C., and mixed until homogeneous. The mixture was cooled to 60 to 65° C. while mixing. The ingredients of phase B were combined and added to the main kettle containing phase A. The mixture was cooled to 40 to 45° C., and phase C was added with mixing. The mixture was homogenzied and allowed to cool. At 20 to 25° C., the ingredients of phases D, F, and G were added to the main kettle in succession followed by homogenization after each addition.

Protocol for Measuring In Vitro Optical Properties of Compositions Protocol

A BYK Gardner automatic draw-down instrument was used to produce 25 micron-thick films of the test formulas on 50 micron-thick polyethylene substrates. The films were dried for one hour at room temperature.

Haze was measured using BYK-Gardner Haze-Gard haze meter. Homogenizing power was measured using a Konica Minolta CR-400 chroma meter. All measurements were made in triplicate, with one measurement made on each of three films. Triplicate readings were averaged. The results are summarized in Table 3.

TABLE 2

In Vitro Optical Parameters

| Composition | Haze (%) | Homogenizing Power (x20) | Transparency (%) | Whitening |
|---|---|---|---|---|
| Example 1 (Inventive) | 93.90 (±1.71) | 34.50 (±0.74) | 84.93 (±0.04) | 13.05 (±0.04) |
| Example 2 (Inventive) | 70.27 (±3.08) | 33.67 (±0.84) | 85.29 (±0.15) | 13.02 (±0.03) |
| Example 3 (Inventive) | 70.27 (±0.06) | 7.33 (±0.04) | 86.27 (±0.06) | 12.61 (±0.10) |
| Example 4 (Inventive) | 90.17 (±1.00) | 34.27 (±0.75) | 85.50 (±0.15) | 13.49 (±0.13) |
| Example 5 (Comparative) | 93.93 (±0.15) | 36.47 (±1.79) | 63.36 (±17.55) | 14.87 (±0.14) |
| Example 6 (Comparative) | 73.57 (±27.60) | 32.99 (±1.44) | 85.83 (±0.47) | 13.04 (±0.47) |

Values in parenthesis are the standard deviations of the raw values. Homogenizing power was scaled by a multiplication of twenty.

From the results in Table 3 above, it was found that, Examples 1 and 4, yielded the highest values for haze, homogenizing power, and whitening while having the lowest values for whitening. Haze and homogenizing power are directly related to the ability of the composition to decreasing the visibility of fine lines and deep wrinkles. Transparency values directly correlate to translucent/transparent or natural appearance on the skin. Whitening is a measure of the white cast that appears on the skin after the product is applied. Whitening is an undesirable characteristic for the compositors of the present invention, and lower values are desired.

What is claimed is:

1. A cosmetic skin care composition comprising:
   (a) about 10% to about 20% by weight, based upon the total weight of the composition of a film forming agent chosen from interpenetrating polymer network polymers that comprise at least one acrylic polymer and at least one polyurethane;
   (b) about 5% to about 25% by weight, based upon the total weight of the composition of a particulate material that comprises a polyester monomer;
   (c) two or more thickening agents selected from the group consisting of polysaccharide biopolymers and cross-linked anionic acrylamide/AMPS copolymers, wherein the polysaccharide polymer comprises from about 0.01% to about 5.0%, based upon the total weight of the composition;
   (d) about 55% to about 80% by weight, based upon the total weight of the composition of water; and
   (e) one or more cosmetically acceptable ingredients;
   wherein the cosmetic composition is topically applied onto skin of a subject in need of the application to reduce the visibility of imperfections and to impart on the skin a homogenizing effect and a transparency effect of about 83% to about 88%, and
   wherein the film forming agent (a) is present in an amount sufficient to impart a haze effect on the skin up to about 98%.

2. The cosmetic skin care composition of claim 1 wherein the film forming agent, (a), is polyurethane-2 (and) polymethyl methacrylate (INCI name).

3. The cosmetic skin care composition of claim 1 wherein the particulate material that comprises a polyester monomer is known by the INCI name adipic acid/neopentyl glycol crosspolymer.

4. The cosmetic skin care composition of claim 1 wherein the polysaccharide biopolymer is xanthan gum.

5. The cosmetic skin care composition of claim 1 wherein the crosslinked anionic acrylamide/AMPS copolymers is known by the INCI name polyacrylamide (and) C13-14 isoparaffin (and) laureth-7.

6. The cosmetic skin care composition according to claim 1 wherein the crosslinked anionic acrylamide/AMPS copolymers comprises from about 0.5% to about 10%, based upon the total weight of the composition.

7. The cosmetic skin care composition according to claim 1 comprising from about 14% to about 16% film forming agent, to impart a haze effect of about 85% to about 98%.

8. A method for reducing the visibility of imperfections and/or to imparting homogenizing effect on the skin, comprising topically applying onto skin of a subject in need of the application a cosmetic composition comprising:
   (a) about 10% to about 20% by weight, based upon the total weight of the composition of a film forming agent chosen from interpenetrating polymer network polymers that comprise at least one acrylic polymer and at least one polyurethane;
   (b) about 5% to about 25% by weight, based upon the total weight of the composition of a particulate material that comprises a polyester monomer;
   (c) two or more thickening agents selected from the group consisting of polysaccharide biopolymers and cross-linked anionic acrylamide/AMPS copolymers, wherein the polysaccharide polymer comprises from about 0.01% to about 5.0%, based upon the total weight of the composition; and
   (d) about 55% to about 80% by weight, based upon the total weight of the composition of water; and
   (e) one or more cosmetically acceptable ingredients;
   wherein the cosmetic composition as topically applied onto skin of a subject imparts to the skin a homogenizing effect and a transparency effect of about 83% to about 88%, and
   wherein the film forming agent (a) is present in an amount sufficient to impart a haze effect on the skin up to about 98%.

9. The cosmetic skin care composition of claim 1 wherein the crosslinked anionic acrylamide/AMPS copolymer thickening agent comprises from about 5% to about 7% by weight, based upon the total weight of the composition.

10. A cosmetic skin care composition comprising:
   (a) about 15% to about 25% by weight, based upon the total weight of the composition of a film forming agent comprising a mixture of two interlaced polymers that comprise at least one acrylic polymer and at least one polyurethane;
   (b) about 5% to about 25% by weight, based upon the total weight of the composition of a particulate material that comprises a polyester monomer;
   (c) two or more thickening agents selected from the group consisting of polysaccharide biopolymers present from about 0.01% to about 5.0% by weight, based upon the total weight of the composition, and crosslinked anionic acrylamide/AMPS copolymers present from about 5% to about 7% by weight, based upon the total weight of the composition;
   (d) water present from about 55% to about 80% by weight, based upon the total weight of the composition; and
   (e) one or more cosmetically acceptable ingredients;
   wherein the cosmetic composition is topically applied onto skin of a subject in need of the application to reduce the visibility of imperfections and to impart on the skin a homogenizing effect and a transparency effect of about 83% to about 88%, and a haze effect of about 85% to about 98%.

* * * * *